(12) United States Patent
Gary, Jr. et al.

(10) Patent No.: US 8,410,926 B1
(45) Date of Patent: Apr. 2, 2013

(54) ALARM FOR SECURITY TAG

(75) Inventors: Wyndham F. Gary, Jr., Whitefish Bay, WI (US); Jeff Krueger, Waukesha, WI (US); John LaBorde, Oconomowoc, WI (US)

(73) Assignee: RF Technologies, Inc., Brookfield, WI (US)

(*) Notice: Subject to any disclaimer, the term of this patent is extended or adjusted under 35 U.S.C. 154(b) by 414 days.

(21) Appl. No.: 12/776,275

(22) Filed: May 7, 2010

(51) Int. Cl.
*G08B 1/08* (2006.01)
*G08B 23/00* (2006.01)
*A61B 5/00* (2006.01)
*A44C 5/00* (2006.01)

(52) U.S. Cl. ........... 340/539.12; 340/539.31; 340/572.1; 340/573.1; 40/299.01; 600/301

(58) Field of Classification Search ............. 340/539.12, 340/539.31
See application file for complete search history.

(56) References Cited

U.S. PATENT DOCUMENTS

| | | | |
|---|---|---|---|
| 4,812,823 A | 3/1989 | Dickerson | |
| 4,885,571 A | 12/1989 | Pauley et al. | |
| 4,952,913 A | 8/1990 | Pauley et al. | |
| 5,032,823 A | 7/1991 | Bower et al. | |
| 5,075,670 A | 12/1991 | Bower et al. | |
| 5,504,474 A | 4/1996 | Libman et al. | |
| 5,512,879 A | 4/1996 | Stokes | |
| 5,541,580 A | 7/1996 | Gerston et al. | |
| 5,731,757 A | 3/1998 | Layson, Jr. | |
| 5,831,535 A | 11/1998 | Reisman et al. | |
| 5,936,529 A | 8/1999 | Reisman et al. | |
| 5,959,533 A | 9/1999 | Layson, Jr. et al. | |
| 5,977,877 A | 11/1999 | McCulloch et al. | |
| 5,982,281 A | 11/1999 | Layson, Jr. | |
| 6,014,080 A | 1/2000 | Layson, Jr. | |
| 6,084,513 A | 7/2000 | Stoffer | |
| 6,144,303 A | 11/2000 | Federman | |
| 6,405,213 B1 | 6/2002 | Layson et al. | |
| 6,639,516 B1 | 10/2003 | Copley | |
| 6,774,799 B2 | 8/2004 | Defant et al. | |
| 6,847,892 B2 | 1/2005 | Zhou et al. | |
| 6,853,304 B2 | 2/2005 | Reisman et al. | |
| 6,977,586 B2 | 12/2005 | Martin et al. | |
| 6,992,581 B2 | 1/2006 | Reisman et al. | |
| 6,998,985 B2 | 2/2006 | Reisman et al. | |
| 7,064,670 B2 | 6/2006 | Galperin et al. | |
| 7,119,695 B2 | 10/2006 | Defant et al. | |
| 7,132,944 B1 | 11/2006 | Kron et al. | |
| 7,205,890 B2 | 4/2007 | Defant et al. | |

(Continued)

FOREIGN PATENT DOCUMENTS

CA 2 473 983 1/2006
GB 2 415 072 B 6/2008

(Continued)

*Primary Examiner* — Donnie Crosland
(74) *Attorney, Agent, or Firm* — Foley & Lardner LLP

(57) ABSTRACT

A security system can include a tag unit adapted to be secured to an infant via band. The first tag unit can include a temperature sensor, and a capacitance sensor. A temperature alarm can be provided in response to a negative slope of a temperature curve associated with temperature data from the temperature sensor. A capacitance alarm can be provided in response to a comparison to capacitance data from the capacitance sensor to a baseline when the tag unit is not secured to the infant. A resistance alarm can be provided in response to resistance data indicating a spike in resistance followed by a relatively flat line response.

20 Claims, 11 Drawing Sheets

U.S. PATENT DOCUMENTS

| | | |
|---|---|---|
| 2003/0109988 A1 | 6/2003 | Geissler et al. |
| 2004/0021569 A1 | 2/2004 | Lepkofker et al. |
| 2004/0252015 A1 | 12/2004 | Galperin et al. |
| 2008/0301853 A1 * | 12/2008 | Cummiskey et al. ............. 2/170 |

FOREIGN PATENT DOCUMENTS

| | | |
|---|---|---|
| WO | WO 01/63318 A1 | 8/2001 |
| WO | WO 2007/017855 A1 | 2/2007 |

* cited by examiner

ALARM FOR SECURITY TAG

BACKGROUND

The present application relates to security systems. More particularly, the system relates to a security system including tags that are attached to a person or article.

Security systems are often utilized to protect persons and/or articles from unauthorized movement or theft. Security systems can utilize an active or passive tag that is attached to a person or article. In one exemplary application, tags are secured to infants or other patients to prevent their removal from locations within the medical facility without authorization.

The possible abduction of an infant or child from medical facilities, such as hospitals, other medical structures, temporary housing and other restricted areas has created a significant demand for monitoring systems which signal any unwarranted movement of the infant or child from the assigned environment or area. The standard method used heretofore, such as visitor passes, monitoring cameras, and standard door monitors have not provided the necessary protection against such unwarranted movement of personnel, and particularly an infant or child, from an assigned or restricted area. Hospitals and like facilities are thus continuously looking for improved systems which will essentially prevent unwarranted movement and abduction of an infant or child, thereby maintaining a very safe and secure environment for the infants and other such personnel. The systems and methods may, of course, be applied to other persons or objects and other security applications.

Conventional infant security systems, such as SafePlace® Solution manufactured by RF Technologies, Inc., assignee of the present application, include an RF tag that is secured to the monitored infant via a band. The RF tag communicates with receivers located throughout a restricted area. The receivers are responsive to the RF tag and can be coupled to one or more controllers. The controllers can lock or otherwise control an egress or ingress (such as a door, hall, elevator, or the like) to the restricted area in response to the signal from the RF tag. The receivers can also provide an alarm or provide a signal to an alarm controller or central station (e.g., a nurses' station). The receivers are generally mounted to a wall, ceiling, or other similar locations and are hard wired to a controller or communicate wirelessly with the controller and/or nurses' station.

Generally, the RF tag can be removed from the infant by cutting or breaking the band. The RF tag generally includes a tamper alarm that provides a signal or alarm if the band is cut by detecting a current that flows through the band. When the band is cut or removed, an open band condition is detected and a signal to the central station or an alarm is produced Tags are banded snugly to the infant to prevent them from slipping off an infant's ankle or wrist. However, transmitters can slip off the ankle or wrist or otherwise be removed without cutting the band. Newborn infants can lose water weight six to eighteen hours after birth, and this loss of weight may allow the band and transmitter to slip off the ankle or wrist. Most hospitals have instructed nurses to check and adjust the band for the proper tension every time they handle an infant as part of standard operating procedures. Facilities using current systems can create reminders in the software to adjust the infant band at 1-24 hours after initial banding. However, since this process may not be practical for all facilities, the need still exists for an alarm that indicates when a tag slips off, is cut, or otherwise removed.

Thus, there is a need for a security system that more effectively detects when an RF tag has been removed, intentionally or unintentionally, from a person or object. There is also a need to detect when a tag has been removed from a person or object without significant false alarms.

Further, there is a need for a banding material for RF tags that is optimized for use for persons such as infants. Still further, there is a need for circuits, software, or combinations thereof that detect the removal of a tag from an person. Yet further, there is a need for an algorithm that utilizes several characteristics to determine whether a tag unit has been removed, intentionally or unintentionally from a person or object and provides an alarm indication or message.

SUMMARY

One embodiment relates to an infant security system. The security system includes a tag unit adapted to be secured to an infant via band. The first tag unit includes a temperature sensor and a capacitance sensor. A temperature alarm is provided in response to a negative slope of a temperature curve associated with temperature data from the temperature sensor. A capacitance alarm is provided in response to a comparison to capacitance data from the capacitance sensor to a baseline when the tag unit is not secured to the infant. A resistance alarm is provided in response to resistance data indicating a spike in resistance associated with the band followed by a relatively flat line response.

Another embodiment relates to a tag including a band for securing to a person via the band. The tag including control circuitry receiving a temperature signal from a temperature sensitive component, a capacitive signal from a capacitive element and resistance signal associated with the band. The control circuitry provides at least one of a temperature alarm in response to a negative slope of a temperature curve associated with the temperature signal, a capacitance alarm in response to a comparison to capacitance signal associated with the capacitive element to a baseline, and a resistance alarm in response to resistance signal having a spike followed by a relatively flat line response Still another embodiment relates to a method of determining a security alarm indication that a tag has been removed from a person. The method includes providing a temperature signal associated with a temperature of the tag; providing a capacitance signal associated with a capacitive element of the tag; and providing a resistive signal associated with the resistance across the band. The method further includes providing the security alarm indication in response to at least one of a negative slope of a temperature curve associated with the temperature signal, in response to a comparison of the capacitance signal to a baseline when the tag unit is not secured to the person, and in response to the resistance signal indicating a spike in resistance followed by a relatively flat line response.

Yet another embodiment relates to a band for a tag unit in a security system. The tag unit is secured to a human via the band. The band includes a strip of band material having a width of approximately 0.56 inches and a thickness of approximately 0.03 inches. The band material is a woven material and is able to withstand a static force of at least 30 pounds without tearing. The band material has a resistance of 110 ohms per quarter inch of stretch.

It is to be understood that both the foregoing general description and the following detailed description are exemplary and explanatory only, and are not restrictive of the invention as claimed.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION

Figure 1:
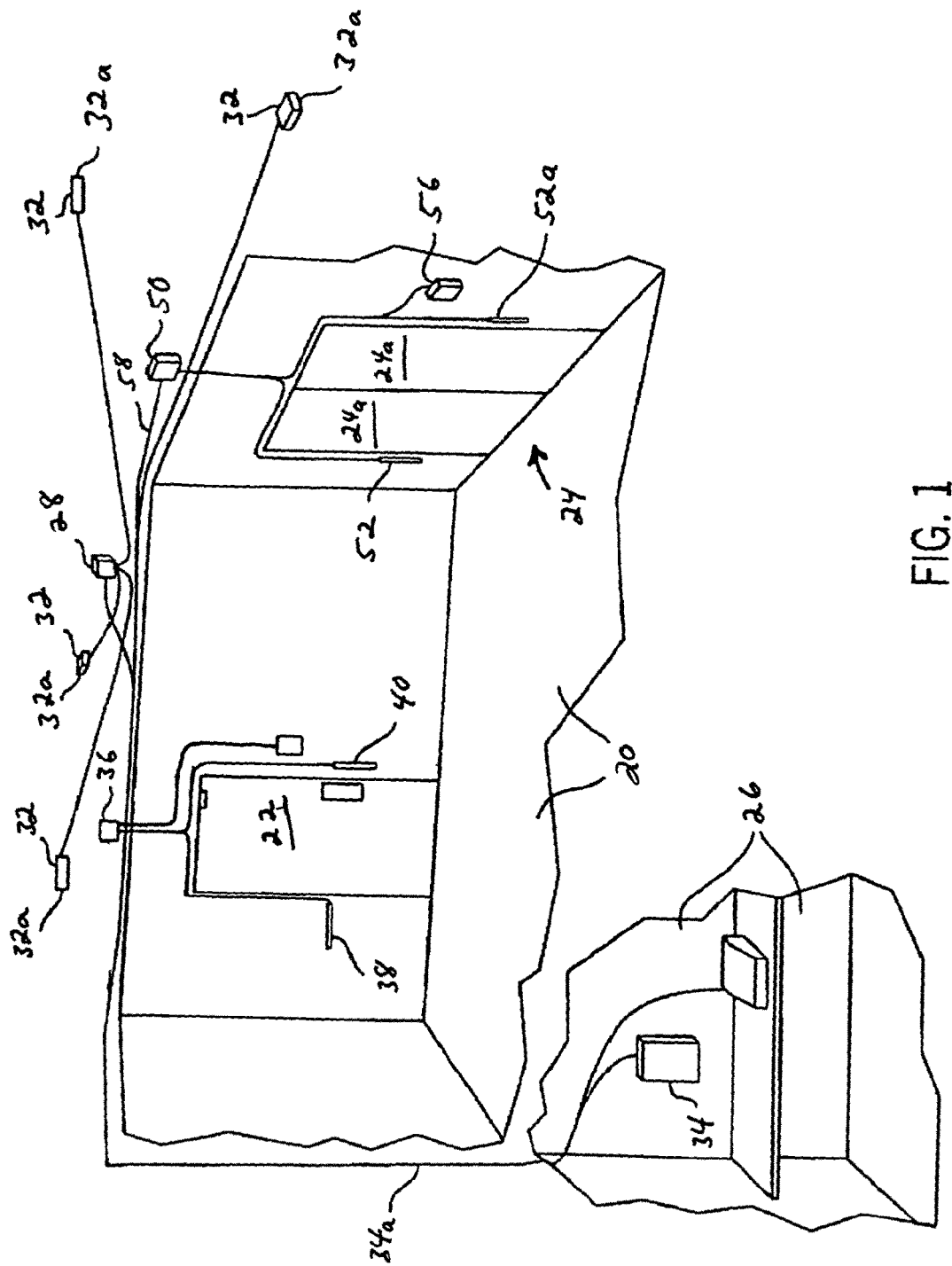
FIG. 1 is a diagrammatic illustration of a secure area incorporating a security system for use with a security tag constructed in accordance with an exemplary embodiment.

Before describing, in detail the particular improved system and method, it should be observed that the invention includes, but is not limited to a novel structural combination of conventional data/signal processing components and communications circuits, and not in the particular detailed configurations thereof. Accordingly, the structure, methods, functions, control and arrangement of conventional components and circuits have, for the most part, been illustrated in the drawings by readily understandable block representations and schematic diagrams, in order not to obscure the disclosure with structural details which will be readily apparent to those skilled in the art, having the benefit of the description herein. Further, the invention is not limited to the particular embodiments depicted in the exemplary diagrams, but should be construed in accordance with the language in the claims.

In general, a security system disclosed herein uses security tags to monitor an object or a person. In one exemplary embodiment, the security tags are used to monitor an infant in medical facilities, such as a hospital. The security tag is intended to reduce the unwarranted movement of personnel, and particularly an infant or child, from an assigned or restricted area. The security tag may also be used, however, to monitor other patients, such as patients with Alzheimer's disease or another form of dementia, or other objects or persons that are not to be moved from secured areas.

An exemplary embodiment is directed to a system having a transmitting monitor or security tag unit coupled to the monitored child that communicates with strategically located receiving units and controllers to respond to alarm signals. Preferably, the tag or tag unit is small and includes a transmitter and an attachment band or strap for attaching the tag unit to the child, other personnel or object to be monitored. The strap is coupled to the transmitting unit such that any removal of or separation within the strap results in the transmission of an alarm signal. The transmitting unit can also transmit a signal to receivers at selected locations and thereby the movement of the banded child can be monitored at certain locations in the restricted area, and particularly near an entry/exit location. Thus, if the alarming strap is cut or tampered with, or just removed without deactivation of the system, an alarm signal is automatically and preferably promptly created. Likewise, if the child wearing the security tag unit moves out of a restricted area, an alarm or alert condition signal is created.

According to an exemplary embodiment, the alarming tag unit includes a battery operated RF transmitter. In a preferred construction, the tag unit includes a lightweight, waterproof transmitting housing connected by a hypoallergenic band or strap for attachment to the child. The strap is interconnected at the opposite ends to the sides of the housing with at least one releasable connector, and preferably opposite strap connectors, to secure the band to the housing and thereby attach the tag unit in a comfortable manner to the child with any excess band trimmed and removed. The transmitter is sealed within the housing, with the circuit connection completed through conduction through the strap. Any opening of the connection to either side or otherwise interfering with the strap, such as cutting of the strap, will trigger an alarm condition. This ensures continuous operation of the transmitter units and response by the system monitors. The receiver units are secured to the entrance/exit locations such as a doorway, hallway, elevator or the like.

The tag unit is battery powered and connects to an electronic banding material. The electronic banding material is used to complete a circuit. The electronic banding material may be used to provide identification information, such as but not limited to patient information to the tag, and/or to other devices. Further, the electronic banding material may be used to encode information such as but not limited to patient information into the electronic banding material. Further still, the electronic banding material may provide an indication if the banding material is disconnected from the tag by tampering or is intentionally removed.

FIG. 1 is a diagrammatic illustration of a medical facility such as a hospital or other area 20 in which infants, children and adult patients may be temporarily housed after birth or while receiving medical care and the like, and which is generally desirably provided with security features to protect from abduction or wandering of the patient, infant, or child. Protected area 20 has a door 22 for entering and exiting the area. Other entrance/exit points might include an elevator 24 with doors 24A. The various rooms and other areas associated with infant care and housing generally include a suitable communication system to a control station, e.g., a nurses' station, a main security station or the like, shown as station 26.

Still referring to FIG. 1, a high frequency controller 28 is mounted, preferably in hidden relation within the secured areas, and includes circuitry responsive to a UHF signal generated by a security tag 30 (see FIG. 2) attached to a child or children within secured area 20. The single UHF controller 28 may control a relatively substantial secured area 20. A plurality of high frequency antenna receivers 32, each with a suitable antenna 32A, may be coupled to controller 28 and distributed throughout secured area 20. If a tag 30 within secured area 20 is removed from the area or tampered with to avoid security, the UHF signal is generated and detected by one or more of the receivers 32 and transmitted to a controller 28, thereby creating an alarm state. The controller 28 can create a visual and/or audible alarm within the immediate secured area in an alarm state. The controller 28 may be connected to a central or control station 26, which has an appropriate monitor 34, including an alarm unit. Generally, the various elements are cabled or hard wired, with hidden wiring, for example as shown by cable 34a. The wiring may be provided with appropriate security to prevent tampering therewith. The elements may also communicate with each other wirelessly.

With continued reference to FIG. 1, a door controller 36 is mounted above door 22, and preferably hidden from view within the wall structure. Low frequency receivers 38 and 40 are located adjacent to door 22 to pick up very low frequency (VLF) signals generated by a tag 30 as a monitored child approaches the door 22. Receivers 38 and 40 can be located to maintain response in the event of one attempting to defeat the security by orientating and shielding the movement of a tag 30 in the field of receivers 38 and 40.

For other exits, such as elevator 24, a separate controller 50 may be provided. As FIG. 1 illustrates, controller 50 is coupled by input cables or wirelessly to a pair of orthogonal low frequency receivers 52A and 52B, which are suitably mounted to opposite sides of elevator doors 24A. The security system for an elevator unit is also typical of any double door unit to a room or area. An elevator door control unit 56 is shown adjacent the elevator and wired to controller 50 and through cable 58 to remote alert unit 34. The control unit 56 includes a suitable alarm and interrelated control.

Figure 2:
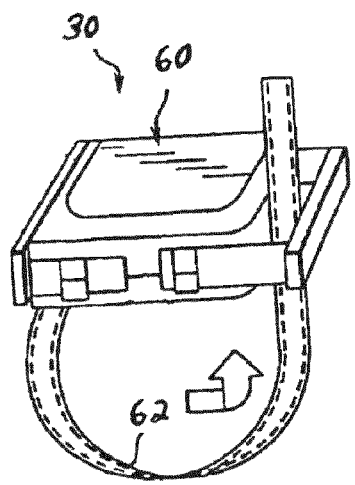
FIG. 2 is a perspective view schematic illustration of a security tag including a band for releasable attachment with a child's limb.

Referring to FIG. 2, security tag 30 is attached to the child. Tag 30 includes a transmitter 60, which is operative to generate radio-frequency (RF) signals. Transmitter 60 can include processors or control circiutry for providing an alarm in response to removal of tag 30. While specific types of RF signals are described, tag 30 can utilize any type of wireless signal. Security tag 30 is secured to the infant by a band 62 (e.g., strap or banding material), which is interconnected to the opposite sides of transmitter 60, and is specially constructed to complete the circuitry of the transmitting circuitry within transmitter 60. Tag 30 is conventionally attached to the wrist, or to the leg immediately above the ankle, of the infant and activated to generate RF signals. In an exemplary construction, transmitter 30 generates a signals for monitoring the exit and entrance of an infant within monitored secured areas 20, and to monitor any removal or other tampering of the attachment of tag 30 on an infant.

Although transmitter 60 may include any desired structure, the structure preferably includes a mechanical interlock between transmitter 60 and band 62. Transmitter unit 60 can include gold teeth or other interface for connecting circuitry within tag 60 to band 62. The circuitry can control the transmitting circuitry and sound an alarm in response to tampering or unauthorized removal of band 62 or tag 30. In one embodiment, area 20 can be monitored by a SafePlace Solution system manufactured by RF Technologies, having tags and a central monitoring station modified in accordance with the functions described herein.

Figure 3A:
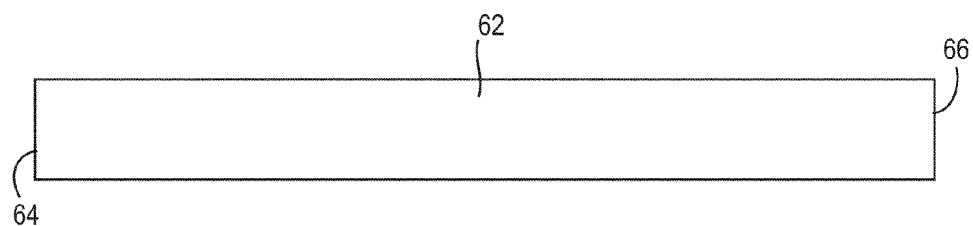
FIG. 3A is a schematic top view schematic illustration of the band for the security tag of FIG. 2 according to an exemplary embodiment.
Figure 3B:
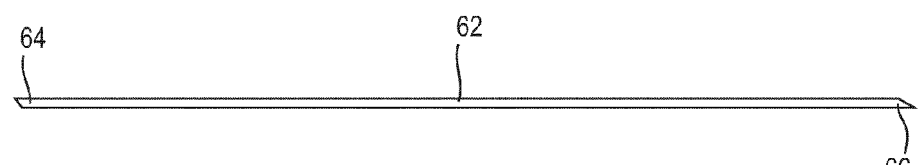
FIG. 3B is a schematic side view schematic illustration of the band for the security tag of FIG. 2 according to an exemplary embodiment.

Referring now to FIGS. 3A and 3B, in an exemplary embodiment, band 62 may have a width of approximately 0.56 inches and a thickness of approximately 0.06 inches. According to one exemplary embodiment, band 62 has a length of approximately 6 inches. The length may be greater or less depending on the application for which the security tag 30 is used. For example, while 6 inches may be a sufficient band length to encircle an infant's wrist or ankle, the length may be greater if the security tag 30 is to be worn by an adult. Band 62 has a first end 64 that is beveled at an angle of 30 degrees and a second end 66 that is beveled at an angle of 60 degrees.

Band 62 is formed of a material that does not contain latex and/or may be configured to include a hypoallergenic material on all exposed surfaces. Band 62 is formed of a woven material and is able to withstand a static force of at least 30 pounds without tearing. Band 62 is formed of a material with a resistance that increases by 110 ohms per quarter inch of stretch. Band 62 preferably has one end cut at a 30 degree angle with respect to parallel sides of band 62 and the opposite end cut at an angle of 60. In a preferred embodiment, band 62 is composed of 3M material number 1229890749-9.

The band 62 may be fastened to the transmitter 60 of the security tag 30 in two separate places to create a circuit. The electronic circuit allows the security tag 30 to detect the presence and absence of the band 62. The circuit creating conduction may be used as an antenna (e.g., for transmitter 60). The circuit creating conduction may also be used to sound an alarm if the circuit is severed (e.g., if band 62 is cut or distorted). Alternatively, tag 30 may use RF energy to read/write/detect band 62.

Security tag 30 further transmits and receives to other RF devices whether banded or not. The transmitted information includes the data from security tag 30 and band 62, as well as the presence or removal of band 62.

Figure 4:
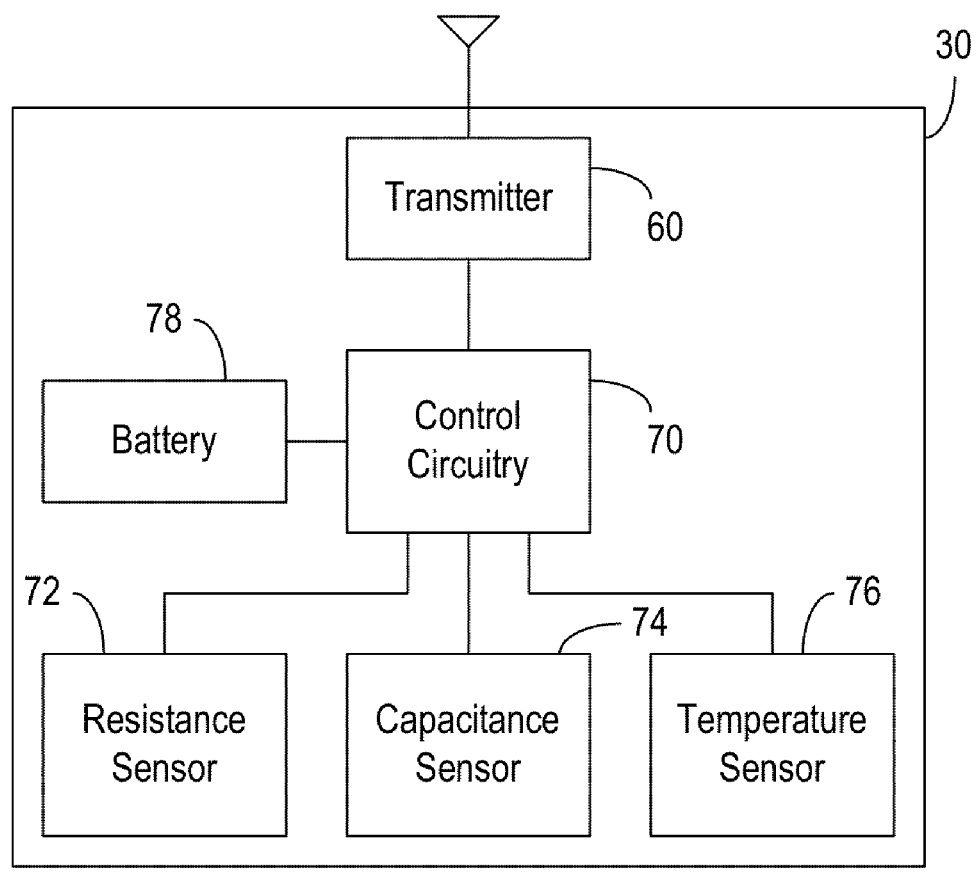
FIG. 4 is a general block diagram of a system for detecting the removal of a security tag according to an exemplary embodiment.

Referring to FIG. 4, security tag 30 includes a system to detect if tag 30 has been removed from the child to which it is attached. The removal may be intentional or may be accidental due to slipping or being inadvertently jostled from the infant's wrist or ankle. The separation of security tag 30 from the infant skin may be determined by accurately and cost effectively detecting a variety of criteria, including capacitance, resistance, and temperature.

Relying on any one criteria may prove problematic. For example, using a capacitance measurement alone may cause false alarms if a loose tag 30 is not in direct contact with the skin. Therefore, security tag 30 is configured to sense multiple criteria when determining if security tag 30 has been removed from the infant. According to an exemplary embodiment, security tag 30 includes a battery or other power source 78 and control circuitry 70 that receives input from a resistance sensor 72, a capacitance sensor 74, and a temperature sensor 76. Circuitry 70 can be hardwired, software executed on processors or combinations thereof without departing from the scope of the invention. Sensors 72 and 76 are in communication with or have elements coupled to band 62. In a preferred embodiment, temperature sensor 76 is within the housing of unit 60. In other embodiments, temperature sensor could be provided on band 62 or have an element coupled to band 62. In other embodiments, sensors 72, 74, and 76 may be provided as separate units that are coupled to a portion of tag 30 or may be provided as remote units that communicate with tag 30 via wired leads or wireless signals. Any type of sensor 72, 74, and 76 can be utilized without departing from the scope of the invention.

Resistance sensor 72 can utilize band 62 and circuitry 70. Resistance is detected by passing a current through the electronic circuit including band 62. The resistance can be determined using voltage and/or current across band 62. Band 62 is formed of a material with a variable resistance, depending on the extent to which band 62 is stretched. According to an exemplary embodiment, band 62 is formed of a material with a resistance of 110 ohms per quarter inch of stretch. Measuring the resistance of band 62 formed of a material with stretch-dependent resistance allows the system to easily detect when and to what extent band 62 is stretched. Further, measuring the resistance of band 62 provides a countermeasure to several methods that may be attempted to bypass the security system. For example, it may be attempted to cut band 62 while band 62 is underwater or short circuited with another conductor. In either case, a system relying only on the detection of a completed circuit may be unable to detect a cut band 62. However, such a circuit will have a smaller resistance than a circuit passing through band 62, allowing such a measure to be detected.

According to an exemplary embodiment, capacitance is measured using a capacitor that is coupled to security tag 30. Capacitive sensor 74 can include two capacitive plates on an inside surface of the housing next to the infant's skin when tag 30 is banded. The capacitance value changes with proximity of security tag 30 to the infant's or other monitored person's skin.

Temperature sensor 76 can be a resistive temperature sensitive element or any other temperature sensitive element coupled to circuitry 70. Assuming a room temperature of 75 F+/−5 F and a body temperature of the infant arm or leg of 98 F+/−5 F, the temperature can be used to determine if security tag 30 is attached to the infant or has been removed and is laying on the floor or bed. According to various exemplary embodiment, the temperature may be sensed using a variety of methods (e.g., detection inside of transmitter 60, detection using direct contact temperature, detection using remote temperature, etc.). Applicants believe that significant temperature changes can readily be detected without the need for a direct skin contact. Therefore, the temperature sensor may be provided on any part of security tag 30. An exemplary system for detecting the removal of security tag 30 using temperature measurements compensates for several factors, including the response time of temperature measurement, the potential drop in temperature associated with the removal of the infant from an incubator, the potential drop in temperature if the infant loses weight and the tag no longer lays snugly against the skin of the wrist or ankle, and the placement of a removed security band in a warm pocket or under warm blankets.

Sensing a temperature difference can be useful in wander management applications. For example, security tag 30 may be utilized in a medical facility for patients suffering from Alzheimer's disease, another form of dementia, or another disease that may cause mental or physical impairment. In such an application, a security tag 30 capable of monitoring temperature can relatively quickly indicate of if a patient is outdoors in relatively cold or hot temperatures.

Alert or alarm events may be triggered by data received from any one of resistance sensor 72, capacitance 74, or temperature sensor 76. In general, data from the sensors 72, 74, and 76 is collected; the data is analyzed to determine if any of the criteria indicate an alarm condition; and a decision is made whether or not to trigger an alarm condition. In one embodiment, control circuitry 70 may analyze data received from resistance sensor 72, capacitance 74, and temperature sensor 76; determine that an alarm condition is indicated by any one of the sensors 72, 74, or 76; and then transmit an alarm or "band off" signal or alarm to a remote controller, such as controller 28 or control station 26.

In another embodiment, control circuitry 70 may analyze data received from resistance sensor 72, capacitance 74, and temperature sensor 76 and determine that an alarm condition is indicated by any one of the sensors 72, 74, or 76. Control circuitry 70 may then transmit the indicated alarm conditions (e.g., resisitance alarm, capacitance alarm, temperature alarm) to a remote controller, such as controller 28 or control station 26 so that controller 28 or a user of control station 26 can determine if a "band off" alarm should be raised.

In yet another embodiment, data received from resistance sensor 72, capacitance 74, and temperature sensor 76 may be transmitted directly to controller 28 or control station 26 with transmitter 60. The data may then be analyzed by controller 28 or a user of control station 26 to determine that an alarm condition is indicated by any one of the sensors 72, 74, or 76 and can determine if a "band off" alarm should be raised.

Several state machines are described below that are utilized to determine the state of security tag 30 and whether security tag 30 is properly attached to an infant or other subject or if security tag 30 has been removed, inadvertently or not, from the infant or other subject. In general, "band open" is used to refer to both an open band, such as a band that has been disconnected or cut, as well as to a state in which security tag 30 has been removed from the infant by sliding off of the infant's limb. Likewise, "band closed" is used to refer to a state in which security tag 30 is attached properly to an infant's limb and is seated against the skin of the ankle or wrist.

Figure 5:
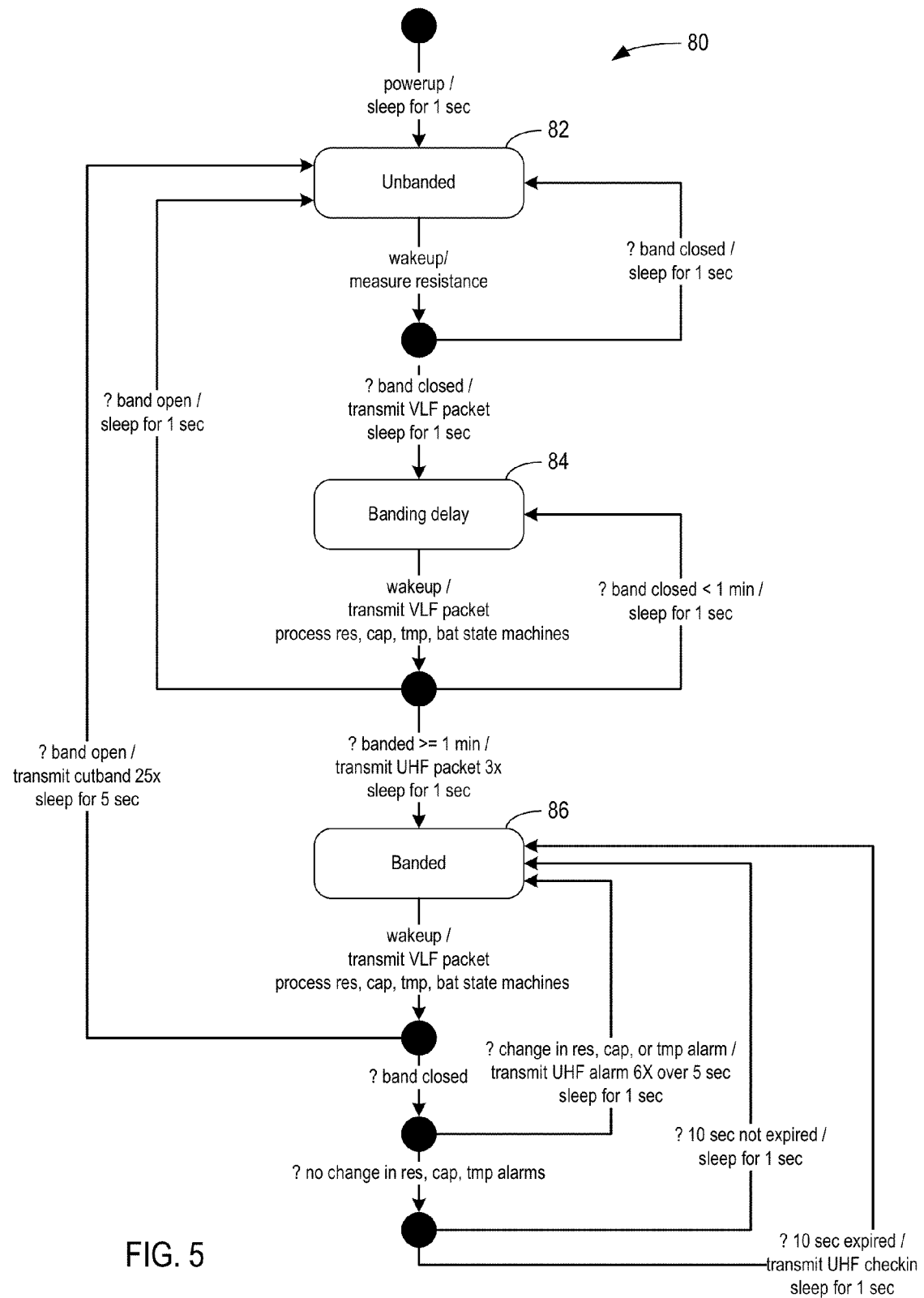
FIG. 5 is a top-level state transition diagram for a system for detecting the removal of a security tag according to an exemplary embodiment.

Referring now to FIG. 5, a state transition diagram is shown according to an exemplary embodiment. The diagram describes a top-level system 80 for determining if a security tag 30 is removed from an infant. When tag 30 is first powered up, system 80 is in a first, unbanded state 82. The resistance is then measured to determine if band 62 is closed. If band 82 is open (e.g., the resistance is found to be very high), system 80 sleeps for one second and then repeats the measurement. No UHF signals are sent in the unbanded state 82. If band 62 is closed (e.g., the resistance drops sharply), system 80 transmits a VLF signal (e.g., a signal sent by transmitter 60 to VLF receiver 28 or 40), sleeps for one second, then transitions to a second, banding delay state 84.

In the banding delay state 84, a VLF packet is transmitted and the resistance, temperature, capacitance, and battery state machines (detailed below) are processed. If the resistance, temperature, or capacitance state machines determine that band 62 is open, system 80 sleeps for one second, then returns to the unbanded state 82. This can occur when a person applying tag 30 to a person or object has unsecured band 62 to adjust the tightness of band 62. After being in the banding delay state 84 for one minute, if the resistance, temperature, and capacitance state machines determine that band 62 is closed, then system 80 transmits three UHF packets (e.g., check in signals sent from transmitter 60 to UHF receiver 32), sleeps for one second, and transitions to a third, banded state 86.

In the banded state 86, a VLF packet is transmitted and the resistance, temperature, capacitance, and battery state machines (detailed below) are processed. If the resistance, temperature, or capacitance state machines determine that band 62 is open (e.g., a cut-band or other security tag removal event), system 80 transmits multiple UHF cut band messages. According to one exemplary embodiment, 25 UHF cut band messages are sent, spaced 200 mS apart. The number and spacing of the messages increase the likelihood that a receiver will receive the cut band message in the presence of multiple security tags or noise. If the resistance, temperature, and capacitance state machines determine that band 62 is closed, system 80 compares the resistance, temperature, or capacitance state machines to previous values to checks if there has been a change. If there is a change in the resistance, temperature, or capacitance state machines, the system transmits six UHF alarm signals over five seconds and sleeps for one second. If there is no change in the resistance, temperature, or capacitance state machines, the system transmits a UHF check in signal every 10 seconds and sleeps for 1 second.

Figure 6:
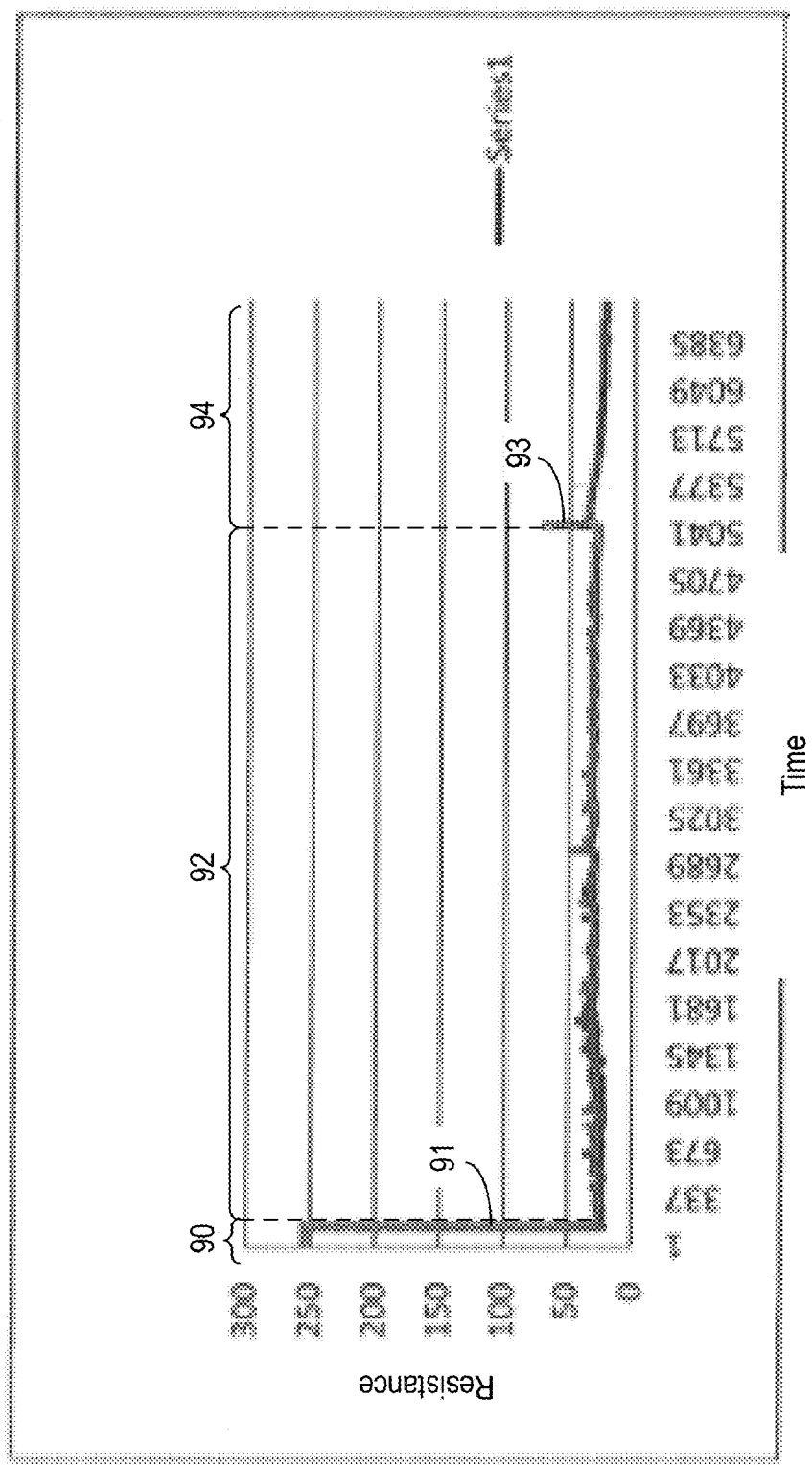
FIG. 6 is a graph of the resistance sensed by a security tag coupled to the ankle of an infant according to an exemplary embodiment.

Referring now to FIG. 6, a graph shows exemplary resistance data collected from a security tag 30 attached to the ankle of an infant over thirty minutes. After thirty minutes, security tag 30 is removed (e.g., slid off the ankle of the infant). Resistance in this thirty minute period can be divided into three segments for analysis. A first segment 90 shows the time period when the security tag is not coupled to the infant. A second segment 92 shows the time period when the security tag is being worn by the infant. A third segment 94 shows the time period after the security tag has been removed from the infant.

First segment 90 is relatively brief and ends with the large drop 91 in resistance. The resistance is high when band 62 is not clamped to both ends of transmitter 60, and drops significantly when band 62 is secured to both sides of transmitter 60. Band 62 has a resistance that changes when it is stretched. If band 62 is stretched when the security tag 30 is initially placed on the infant (e.g., stretched by ⅛" to ¼") and remains in tension when on the infant, then the resistance of band 62 will have a measureable change when security tag 30 is removed from the infant. Second segment 92 includes small changes in resistance resulting from movements of the infant while wearing security tag 30 due to movements of the infant, breathing, etc. The initial banded resistance can very from infant due to the size of the infant's limb, making it infeasible to use a fixed resistance value as a threshold for determining if security tag 30 has been removed. Therefore, a baseline resistance value is automatically calibrated by the system for each infant after the security tag 30 has been attached to the infant.

The third segment 94 begins with a small spike 93 in resistance resulting from band 62 being stretched to allow security tag 30 to be slipped off of the infant's ankle When security tag 30 is removed from the infant and left undisturbed, the steady state resistance change is very small (e.g., a flat-line resistance). The remainder of third segment 94 shows a smooth decrease in resistance which ends in a flat line 95. This sudden change (e.g., spike 93) in resistance followed by a flat line 95 can be used to trigger a resistance alarm. According to one exemplary embodiment, a flat-line 95 is defined as a sliding window of ten samples over ten seconds where adjacent samples differ by no more than a fixed number of A/D (analog to digital converter) counts.

The removal of the security tag 30 by other means from the infant can also be detected by monitoring the resistance. According to one exemplary embodiment, band 62 has a relatively small resistance between 1 to 4000 Ohm. If band 62 is cut underwater, a change in resistance can still be detected. Because band 62 has a minimum base resistance, even when placed on an infant with a very small arm or leg, an external short circuit can also be detected to trigger an alarm. In one embodiment, a sharp reduction in resistance can be used to trigger an alarm.

Figure 7:
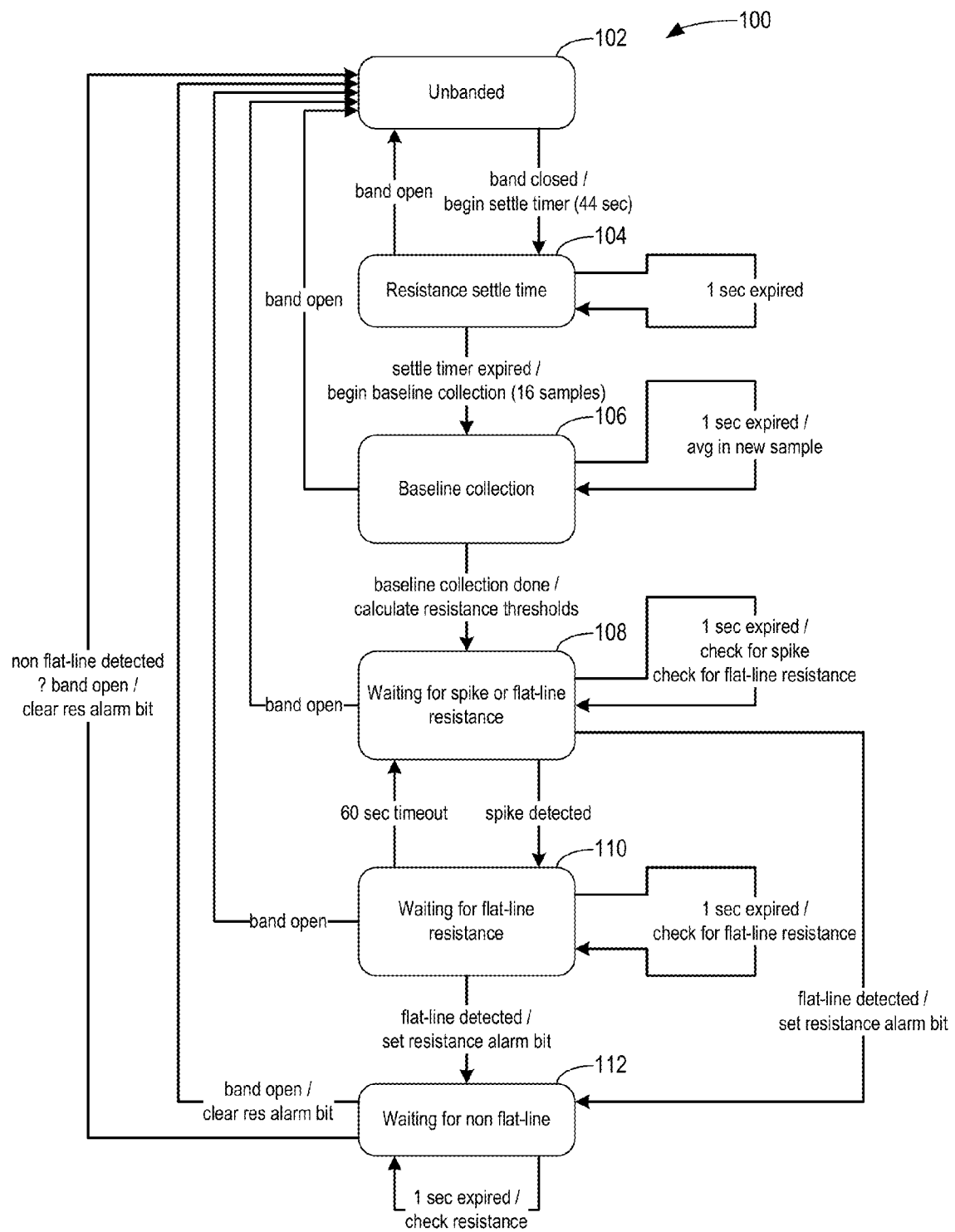
FIG. 7 is a state transition diagram for a system of for detecting the removal of a security tag by sensing electrical resistance according to an exemplary embodiment.

Referring now to FIG. 7, a state transition diagram for a resistance measuring system is shown according to an exemplary embodiment. The system 100 begins in a first, unbanded state 102. Once the band 62 has been closed, the system begins a settle timer and transitions to a second, resistance settle time state 104. According to one exemplary embodiment, the settle timer maintains system 100 in the resistance settle time state 104 for 44 seconds. Once the settle timer expires, system 100 transitions to a third baseline collection state 106. In the baseline collection state 106, a number of resistance samples are taken to establish a customized baseline resistance for a particular infant. According to an exemplary embodiment, sixteen samples are taken during the baseline collection state 106. Each sample is taken one second after the previous sample and immediately averaged in. In other embodiments, the number and frequency of samples along with the method of averaging the samples may vary depending on the precision needs of the system.

Once the baseline resistance is calculated, threshold resistances for determining the removal of the security tag 30 from the infant are calculated and system 100 transitions to a fourth, waiting for spike of flat-line resistance state 108. In the fourth state 108, system 100 checks every second for a spike or flat-line resistance value. If a spike is detected (e.g., the spike 93 that begins the third segment 94 of the resistance graph in FIG. 6), system 100 transitions to a fifth, waiting for flat-line resistance state 110. In the fifth state 110, system 100 continues to check every second for a flat-line resistance value. If a flat-line resistance is detected (e.g., ten consecutive samples with adjacent samples differing by no more than a fixed number of A/D counts as described above), the resistance alarm bit is set and system 100 transitions to a sixth, waiting for non-flat line state 112. System 100 may go directly to the sixth state 112 and bypass the fifth state 110 if a flat-line resistance is detected during the fourth state 108.

In the sixth state 112, system 100 monitors the resistance every second to detect non-flat-line resistance. If a non-flat-line is detected (e.g., due to change in resistance resulting from movement of the banding material), system 100 may transition back to the first, unbanded state 102. During any of the states 104-112, a band open state may be detected (e.g., due to the band being severed, the band being short-circuited, etc.) and the system may transition back to the first, unbanded state 102.

Figure 8:
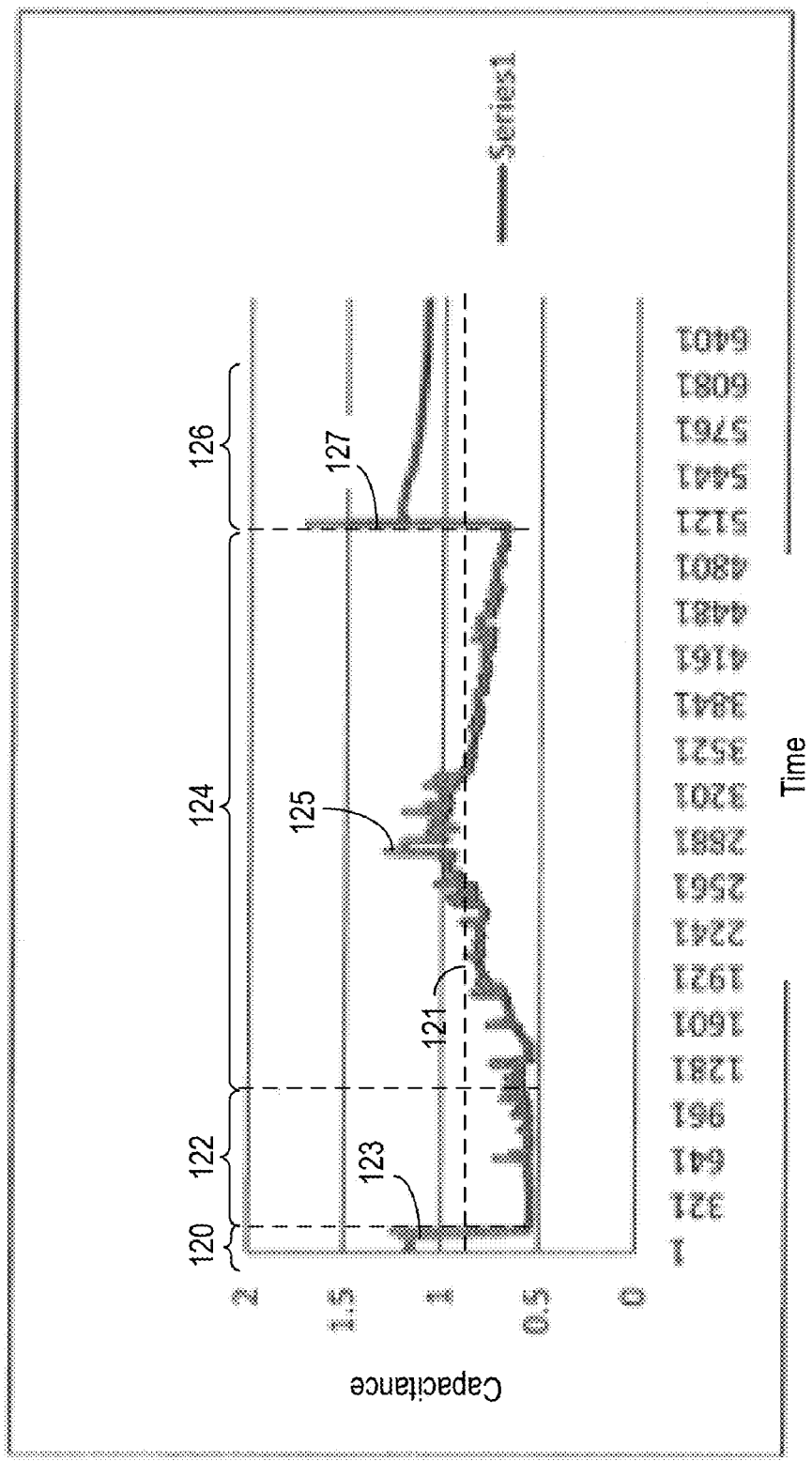
FIG. 8 is a graph of the capacitance sensed by a security tag coupled to the ankle of an infant according to an exemplary embodiment.

Referring now to FIG. 8, a graph shows exemplary capacitance data collected from a security tag 30 attached to the ankle of an infant over thirty minutes. After thirty minutes, security tag 30 is removed (e.g., slid off the ankle of the infant). Capacitance in this thirty minute period can be divided into four segments for analysis. A first segment 120 shows the time period when security tag 30 is not coupled to the infant. A second segment 122 shows the time period when security tag 30 first contacts the infant's skin. A third segment 124 shows the time period when security tag 30 is being worn by the infant. A fourth segment 126 shows the time period after security tag 30 has been removed from the infant.

Measuring the baseline 121 of capacitance in first segment 120 and second segment 122 establishes a threshold above which security tag 30 is no longer in contact with the infant's skin. Second segment 122 begins with a sharp drop 123 in capacitance when band 62 is secured to both sides of transmitter 60 and security tag 30 contacts the infant's skin. During second segment 122, security tag 30 is moved into position and settles against the skin of the infant, resulting in a variable capacitance. Second segment 122 includes small changes in capacitance resulting from movements of the infant while wearing security tag 30 due to movements of the infant, breathing, etc. The capacitance can also vary from infant to infant due to the size of the infant's limb, making it infeasible to use a fixed capacitance value as a threshold for determining if security tag 30 has been removed. The average capacitance of segment 120 and the average capacitance of the segment 122 are used to establish an alarm threshold 121 above which security tag 30 is no longer in contact with the infant's skin. Therefore, a baseline capacitance value is automatically calibrated by the system for each infant after the security tag 30 has been attached to the infant.

After the settling period, during third segment 124, the capacitance may continue to vary with spikes and troughs. Third segment 124 and/or second segment 122 may have a spike 125 above the baseline threshold capacitance 121. An additional requirement for a sustained change past the threshold 121 during second segment 122 and the third segment 124 allows the distinction to be made between infant movements and a true alarm condition. In fourth segment 126, the capacitance may experience another spike 127 and return to the baseline level 121.

Figure 9:
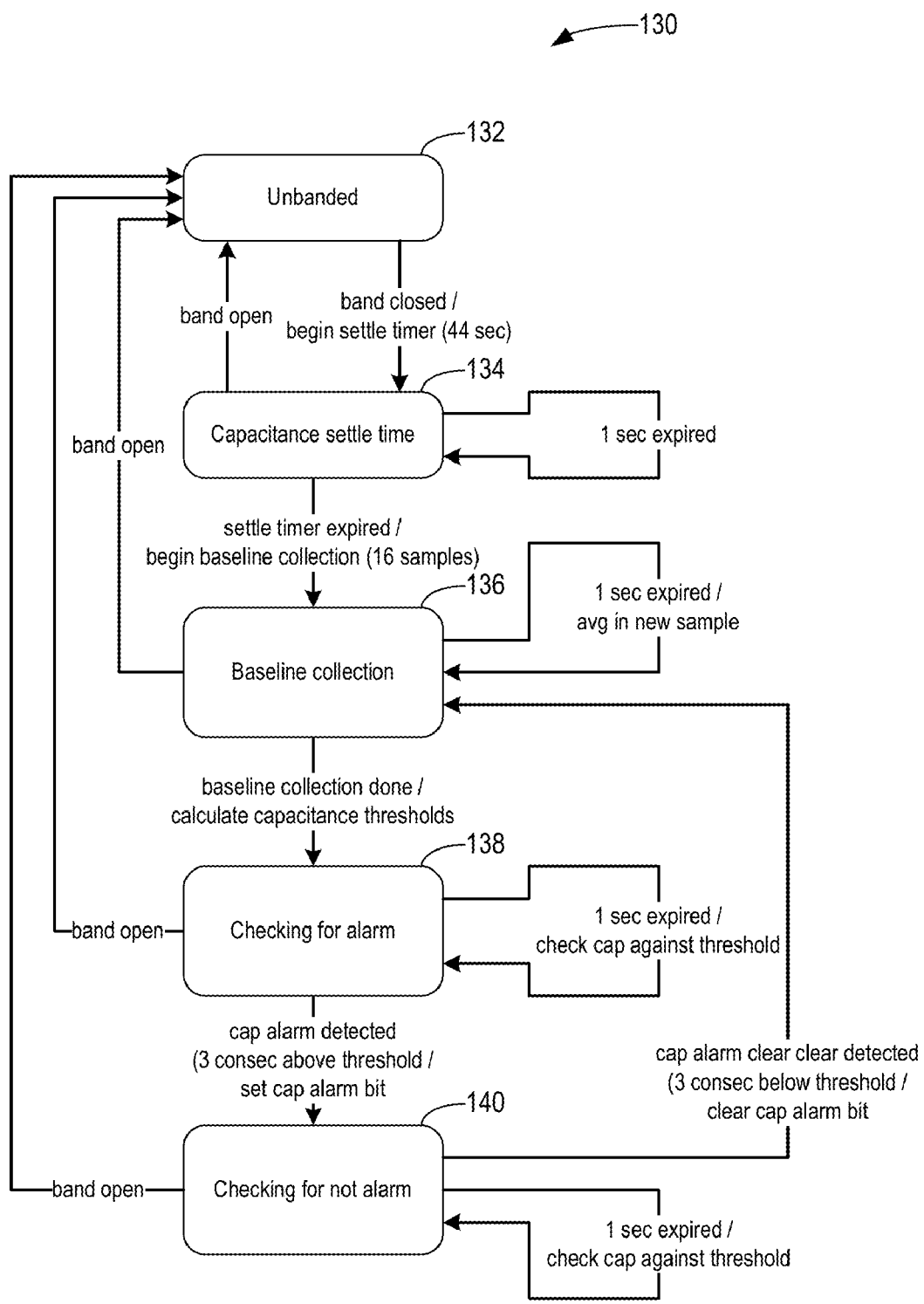
FIG. 9 is a state transition diagram for a system of for detecting the removal of a security tag by sensing capacitance according to an exemplary embodiment.

Referring now to FIG. 9, a state transition diagram for a capacitance measuring system is shown according to an exemplary embodiment. The system 130 begins in a first, unbanded state 132. Once the band 62 has been closed, system 130 begins a settle timer and transitions to a second, capacitance settle time state 134. According to one exemplary embodiment, the settle timer maintains system 130 in the capacitance settle time state 134 for 44 seconds. Once the settle timer expires, system 130 transitions to a third baseline collection state 136. In the baseline collection state 136, a number of capacitance samples are taken to establish a customized threshold capacitance for a particular infant. According to an exemplary embodiment, sixteen samples are taken during the baseline collection state 136. Each sample is taken one second after the previous sample and immediately averaged in. In other embodiments, the number and frequency of samples along with the method of averaging the samples may vary depending on the precision needs of system 130.

Once the baseline capacitance is calculated, threshold capacitances for determining the removal of the security tag 30 from the infant are calculated and system 130 transitions to a fourth, checking for alarm state 138. According to an exemplary embodiment, the alarm threshold capacitance is calculated to be the midpoint between the average capacitance of segment 120 and the average capacitance of segment 122. In the checking for alarm state 138, system 130 checks every second for a capacitance value above the threshold capacitance. If a sustained capacitance exceeding the threshold capacitance is detected, the capacitance alarm bit is set and system 130 transitions to a fifth, checking for not in alarm state 140. According to an exemplary embodiment, system 130 requires three consecutive capacitances above the threshold capacitance to set the capacitance alarm bit. In this way, a distinction can be made between momentary spikes due to infant movements (e.g. a spike 125 in the second segment 122 or third segment 124 of the capacitance graph in FIG. 8) and a true alarm condition.

In the fifth state 140, system 130 monitors the capacitance every second to detect a capacitance below the threshold capacitance. If a sustained capacitance below the threshold capacitance is detected, the capacitance alarm bit is cleared and system 130 transitions back to the third state 136. According to an exemplary embodiment, system 130 requires three consecutive capacitances below the threshold capacitance to clear the capacitance alarm bit. During any of the states 134-140, a band open state may be detected and system 130 may transition back to the first, unbanded state 132.

Figure 10:
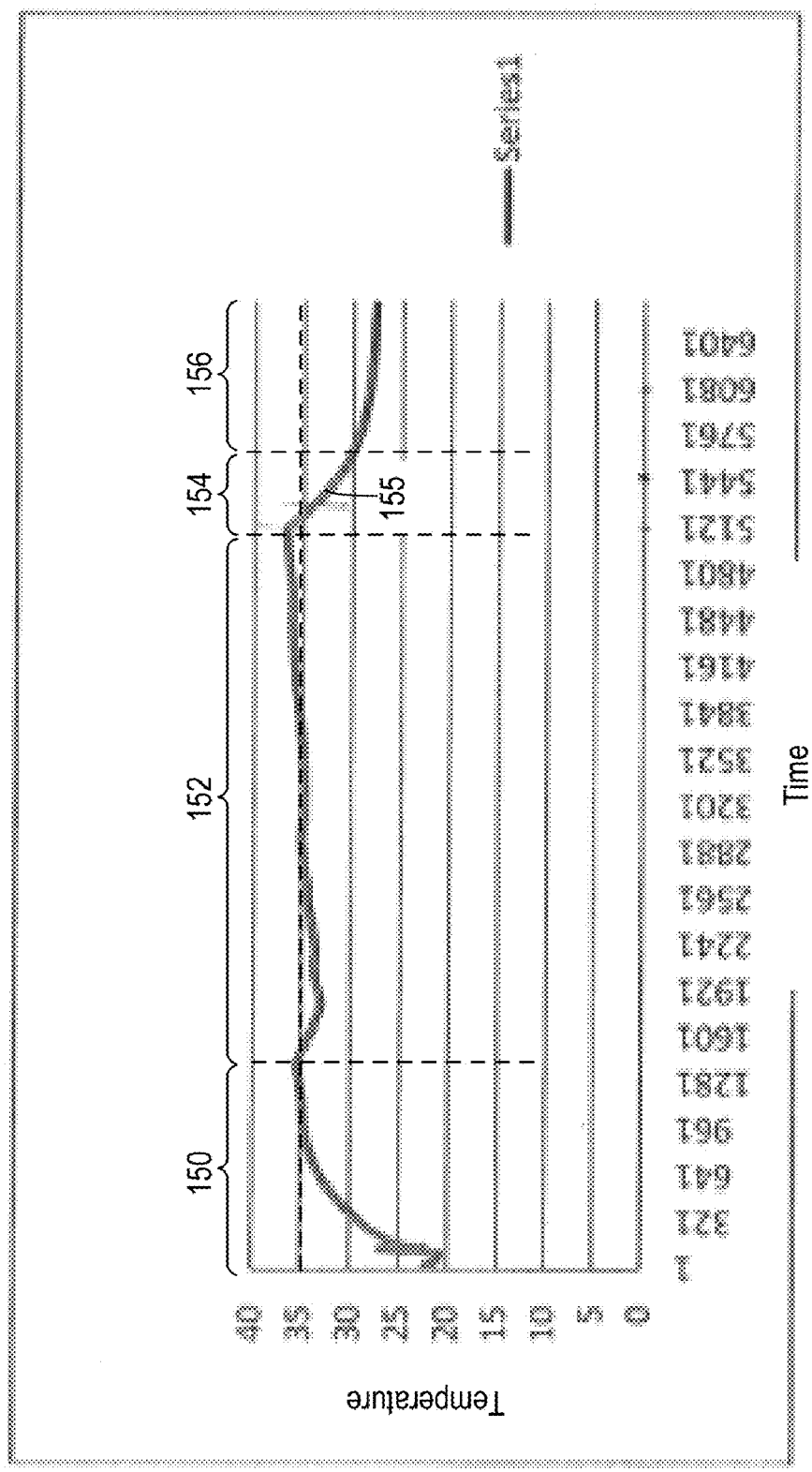
FIG. 10 is a graph of the temperature sensed by a security tag coupled to the ankle of an infant according to an exemplary embodiment.

Referring now to FIG. 10, a graph shows exemplary temperature data collected from a security tag 30 attached to the ankle of an infant over thirty minutes. After thirty minutes, security tag 30 is removed (e.g., slid off the ankle of the infant). Temperature in this thirty minute period can be divided into four segments for analysis. A first segment 150 shows the time period when security tag 30 is initially coupled to the infant. A second segment 152 shows the time period when security tag 30 is in contact with the infant's skin. A third segment 154 shows the time period when security tag 30 is removed from the infant. A fourth segment 156 shows the time period after security tag 30 has been removed from the infant.

During first segment 150 the temperature gradually rises from room temperature to body temperature. During second segment 152, the body temperature experiences normal gradual highs and lows (e.g., based on the baby being swaddled and un-swaddled for changing, the time of day, etc.). During third segment 154, there is a sharp and constant curving decline 155 as security tag 30 is removed. The negative slope of the curve 155 can be configured to trigger an initial temperature alarm. The temperature decline 155 is not instantaneous and must be constant for a minimum of 30 seconds before an alarm is triggered according to one exemplary embodiment to avoid nuisance alarms. During fourth segment 156, there is a well-defined gradual negative slope back to room temperature. After a predetermined time at such a constant gradual slope, translating to a known temperature drop, a temperature alarm can be triggered. For example, 120 seconds at a known slope may equates to over eight degrees of temperature decline.

The relatively stable period in second segment 152 is followed by the initial sharp decline in the third segment 154 and then the steady decline in fourth segment 156. The initial slope of the temperature decline 155 in third segment 154 can be easily identified. Based on the slope alone, an alarm can be triggered. The long steady slope decline in fourth segment 156 can serve as a secondary alarm source as well.

Figure 11:
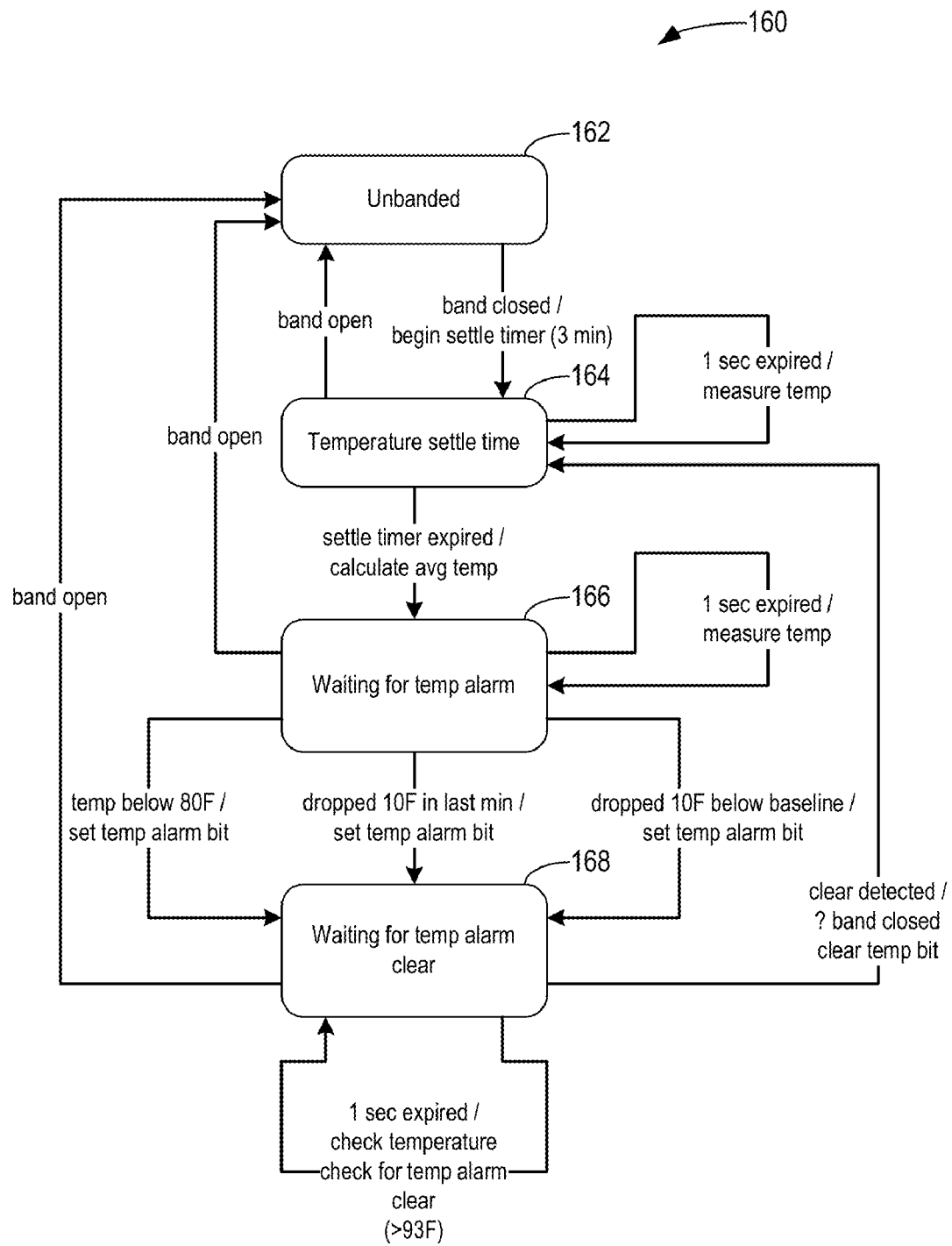
FIG. 11 is a state transition diagram for a system of for detecting the removal of a security tag by sensing temperature according to an exemplary embodiment.

Referring now to FIG. 11, a state transition diagram for a temperature measuring system is shown according to an exemplary embodiment. System 160 begins in a first, unbanded state 162. Once band 62 has been closed, system 160 begins a settle timer and transitions to a second, temperature settle time state 164. According to one exemplary embodiment, the settle timer maintains system 160 in the temperature settle time state 164 for three minutes. In the temperature settle time state 164, system 160 measures the temperature every second. Once the settle timer expires, system 160 calculates an average temperature and transitions to a third, waiting for temperature alarm state 166.

In the third state 166, system 160 checks the temperature every second. If the temperature falls low enough, system 160 sets the temperature alarm bit and transitions to a fourth, waiting for alarm clear state 168. According to an exemplary embodiment, three different events may trigger the temperature alarm. In a first event, the measured temperature falls below a predetermined, static limit (e.g., 80 F). In a second event, the measured temperature is determined to have dropped rapidly from a previously measured temperature value (e.g., 10 F in one minute). In a third event, the measured temperature is determined to have fallen a certain amount below the previously calculated average temperature (e.g., 10 F below the average temperature).

In the fourth state 168, system 160 monitors the temperature every second to detect a temperature above a threshold temperature. If a sustained temperature above the threshold temperature is detected, the temperature alarm bit is cleared and system 160 transitions back to the second state 168. According to an exemplary embodiment, the threshold temperature is set at 93 F. During any of the states 164-168, a band open state may be detected and system 160 may transition back to the first, unbanded state 162.

Figure 12:
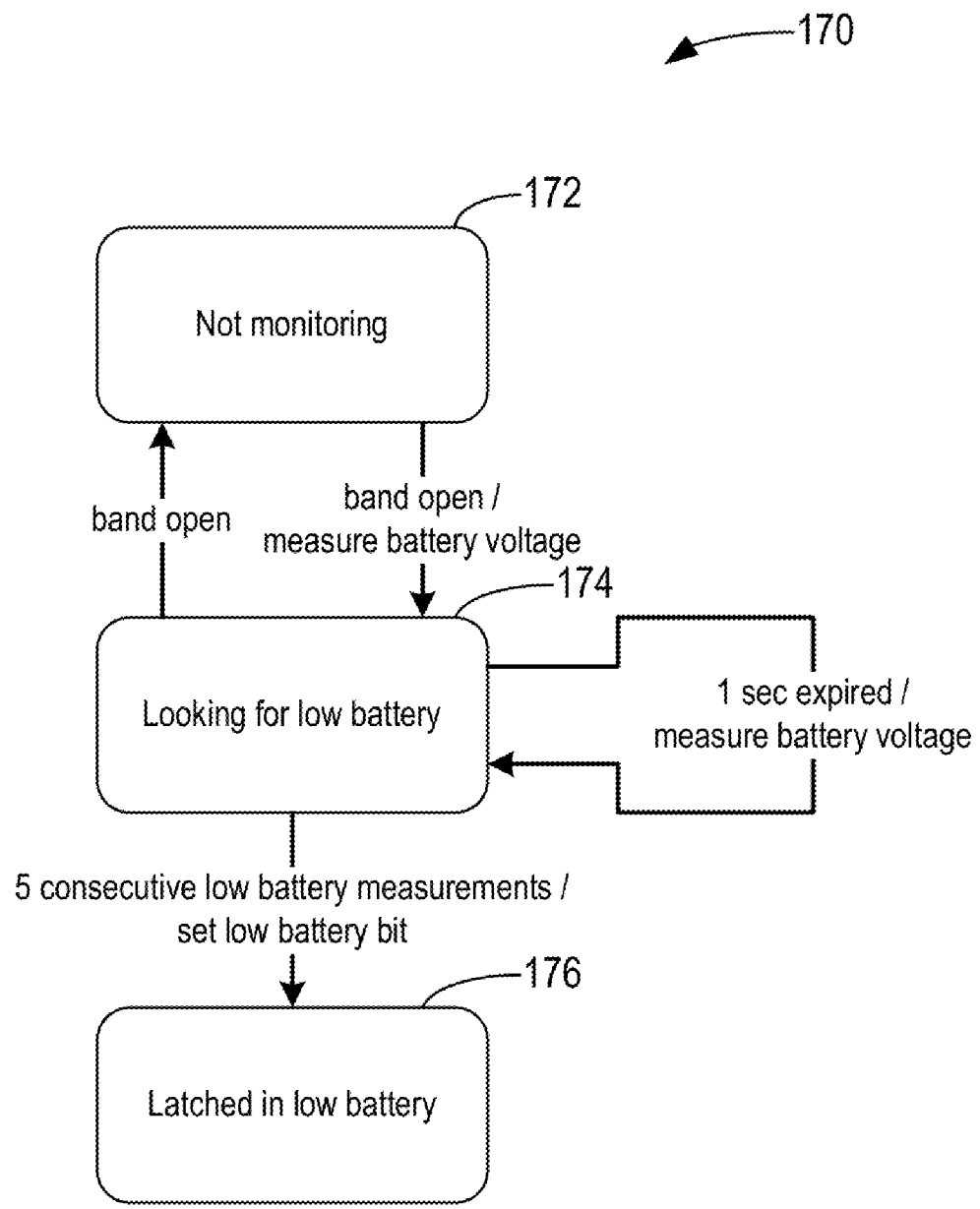
FIG. 12 is a state transition diagram for detecting a low battery condition for a security tag according to an exemplary embodiment.

Referring now to FIG. 12, a state transition diagram for a temperature measuring system is shown according to an exemplary embodiment. The battery voltage is measured each time the microcontroller (e.g., control circuitry 70) wakes up, such as every second while security tag 30 is attached to an infant (e.g., band 62 is closed). According to an exemplary embodiment, the capacitance chip and the microcontroller are rated to operate down to 1.8V. Therefore, the low battery threshold is set at 2.0V. A low battery condition is indicated in the UHF check-in message if the battery voltage has dropped below 2.8V+/−−0.1V for five consecutive measurements.

The system 170 begins in a first, not monitoring state 172. Once band 62 has been closed, system 170 measures the battery voltage and transitions to a second, looking for low battery state 174. If band 62 is open, system 170 transitions back to the not monitoring state 172. In the looking for low battery state 174, system 170 measures the voltage every second. Once the voltage is measure to be below the threshold (e.g., 2.0V) for five consecutive measurements, system 170 sets the low battery bit and transitions to a third, latched in low battery state 176. System 170 remains in the latched in low battery state 176 and reports a low battery message in the UHF check-in message. According to one exemplary embodiment, the receiver (e.g., UHF receiver 32) requires five consecutive low battery messages before notifying a user. Because five seconds are needed to detect five consecutive measurements below the threshold and 50 seconds are needed to transmit five low battery messages once the system is in the third state 176, a minimum of approximately 55 seconds passes before a user is notified of the low battery situation.

It should be understood that the state machines shown in FIGS. 5, 7, 9, 11, and 12 are exemplary only. Any method of programming or software can be utilized to implement the alarm features without departing from the scope of the invention. Security tag 30 may include other processes and logic to process data received to determine if an alarm condition has occurred. Security tag 30 process data using a control circuit, firmware, or processing electronics executing operations, as well as combinations thereof.

For example, settle time periods to compensate for variations due to the initial fastening of band 62 may be shortened or lengthened based on empirical evidence or theoretical calculations to assure that baseline values of capacitance, resistance, and temperature are calculated quickly and accurately enough to reliably diagnose if security tag 30 is attached or detached. Likewise, the frequency with which samples are measured may also be increased or decreased either during programming of the associated device (e.g., control circuitry 70) or may be adaptive and change based on inputs received after band 62 is closed.

A security tag 30 is described above generally as a device worn by an infant. However, the novel method of determining if such a tag has been removed may be applicable to security tags used in other security systems and applications. A security tag 30 may be worn by another person, typically around a wrist or ankle. Persons who may wear tag unit 30 as described above may include, but are not limited to emergency room patients, doctors, nurses, technicians, other hospital personnel. Alternatively tag 30 may be attached to objects. Objects which may have a tag 30 attached include but are not limited to blood tags, medication, equipment, food trays, files, etc. Tag 30 may be used to locate objects and personnel, sound alarms, measure temperature, provide information regarding attendance of personnel, identify proper blood types or medications, etc.

The security tag 30 is described as determining if it has been detached by measuring resistance, capacitance, and temperature. In other exemplary embodiments, security tag 30 may use other criteria determine if it has been detached.

For example, security tag 30 may use diagnostic measurements such as electrocardiography (ECG) data, saturation of peripheral oxygen (SpO2), diagnostic temperature, etc. and may utilize one or more separate cable leads to facilitate measurements. In other exemplary embodiments, other data such as inductance, infrared, or visible light may be used by security tag 30 to determine if it has been detached.

Various embodiments disclosed herein may include or be implemented in connection with computer-readable media configured to store machine-executable instructions therein, and/or one or more modules, circuits, units, or other elements that may comprise analog and/or digital circuit components (e.g. a processor or other processing circuit) configured or arranged to perform one or more of the steps recited herein. By way of example, computer-readable media may include RAM, ROM, CD-ROM, or other optical disk storage, magnetic disk storage, flash memory, or any other medium capable of storing and providing access to desired machine-executable instructions. The use of circuit or module herein is meant to broadly encompass any one or more of discrete circuit components, analog and/or digital circuit components, integrated circuits, solid state devices and/or programmed portions of any of the foregoing, including microprocessors, microcontrollers, ASICs, programmable logic, or other electronic devices.

While the detailed drawings, specific examples and particular formulations given describe preferred and exemplary embodiments, they serve the purpose of illustration only. The inventions disclosed are not limited to the specific forms shown. For example, the methods may be performed in any of a variety of sequence of steps. The hardware and software configurations shown and described may differ depending on the chosen performance characteristics and physical characteristics of the computing devices. For example, the type of computing device, communications bus, or processor used may differ. The systems and methods depicted and described are not limited to the precise details and conditions disclosed. Furthermore, other substitutions, modifications, changes, and omissions may be made in the design, operating conditions, and arrangement of the exemplary embodiments without departing from the scope of the invention.

What is claimed is:

1. An infant security system, comprising:
   a tag unit adapted to be secured to an infant via a band, the tag unit including a temperature sensor, and a capacitance sensor,
   wherein a temperature alarm is provided in response to a negative slope of a temperature curve associated with temperature data from the temperature sensor, a capacitance alarm is provided in response to a comparison of capacitance data from the capacitance sensor to a baseline when the tag unit is not secured to the infant, and a resistance alarm is provided in response to resistance data indicating a spike in resistance followed by a relatively flat line response.

2. The infant security system of claim 1, wherein the temperature sensor is located entirely within the tag unit and does not sense temperature at a skin portion of the infant.

3. The infant security system of claim 1, wherein the resistance alarm, the temperature alarm, and the capacitance alarm are determined by a control circuit within the tag unit.

4. The infant security system of claim 1, wherein the resistance alarm is provided when the resistance data indicates an open circuit.

5. The infant security system of claim 4, wherein the capacitance sensor includes two plates located on an inside surface of a plastic enclosure of the tag unit closest to the infant's skin.

6. The infant security system of claim 1, wherein the negative slope is a relatively consistent slope for at least 30 seconds.

7. The infant security system of claim 1, wherein the negative slope includes an at least 8 degree temperature decline.

8. The infant security system of claim 1, wherein the resistance alarm, the temperature alarm, and the capacitance alarm are determined by a central computer communicating with the tag unit via an RF link.

9. The infant security system of claim 1, wherein the tag unit performs initialization when secured to the infant, the initialization comprising of initialization of capacitance, temperature, and battery state machines.

10. A tag for securing to a person via a band, the tag comprising:
control circuitry receiving a temperature signal from a temperature sensitive component, a capacitance signal from a capacitive element and a resistance signal associated with the band,
wherein the control circuitry provides at least one of a temperature alarm in response to a negative slope of a temperature curve associated with the temperature signal, a capacitance alarm in response to a comparison of the capacitance signal associated with the capacitive element to a baseline, and a resistance alarm in response to the resistance signal having a spike followed by a relatively flat line response.

11. The tag of claim 10 further comprising:
an RF transmitter for providing a message including at least one of the resistance alarm, the temperature alarm, and the capacitance alarm to a central computer.

12. A method of determining a security alarm indication that a tag has been removed form a person, the tag being secured to the person using a band, the method comprising:
providing a temperature signal associated with a temperature of the tag;
providing a capacitance signal associated with a capacitive element of the tag;
providing a resistance signal associated with a resistance across the band; and
providing the security alarm in response to at least one of a negative slope of a temperature curve associated with the temperature signal, in response to a comparison of the capacitance signal to a baseline when the tag unit is not secured to the person, and in response to the resistance signal indicating a spike in resistance followed by a relatively flat line response.

13. The method of claim 12, wherein the person is an infant.

14. The method of claim 12, wherein the band has a variable resistance when stretched.

15. The method of claim 12, further comprising:
providing an RF message to a central station in response to the security alarm.

16. The method of claim 15, wherein the band has width of approximately 0.56 inches and a thickness of 0.06 inches.

17. A tag unit in a security system, the tag unit being secured to a human, the tag unit comprising:
a strip of band material having a width of approximately 0.56 inches and a thickness of approximately 0.06 inches, the band material being woven material and being able to withstand a static force of at least 30 pounds without tearing, the band material having a resistance of 110 ohms per quarter inch of stretch;
a temperature sensor,
a capacitance sensor; and
wherein a temperature alarm is provided in response to a negative slope of a temperature curve associated with temperature data from the temperature sensor, a capacitance alarm is provided in response to a comparison of capacitance data from the capacitance sensor to a baseline when the tag unit is not secured to the human, and a resistance alarm is provided in response to resistance data indicating a spike in the resistance of the band material followed by a relatively flat line response.

18. The tag unit of claim 17, wherein the band material does not include latex.

19. The tag unit of claim 17, wherein the strip has a length of approximately 6 inches.

20. The tag unit of claim 17, wherein the strip has a first end having a first side at a 30 degree angle with respect to parallel sides of the strip and a second end having a second side at a 0 degree angle with respect to the parallel sides of the strip.

* * * * *